United States Patent [19]

Maxey et al.

[11] Patent Number: 5,383,024
[45] Date of Patent: Jan. 17, 1995

[54] OPTICAL WET STEAM MONITOR

[75] Inventors: Lonnie C. Maxey, Powell; Marc L. Simpson, Knoxville, both of Tenn.

[73] Assignee: Martin Marietta Energy Systems, Inc., Oak Ridge, Tenn.

[21] Appl. No.: 267,919

[22] Filed: Jul. 6, 1994

Related U.S. Application Data

[63] Continuation of Ser. No. 928,340, Aug. 12, 1992, abandoned.

[51] Int. Cl.$^6$ ............................................. G01N 15/02
[52] U.S. Cl. ...................... 356/336; 356/342; 356/28.5; 356/349
[58] Field of Search ............ 356/28.5, 5, 318, 335–343, 356/349, 353, 354, 356; 250/574, 222.2; 73/861.06

[56] References Cited

U.S. PATENT DOCUMENTS

| | | | |
|---|---|---|---|
| 3,302,027 | 1/1967 | Fried et al. | 356/349 |
| 3,523,735 | 8/1970 | Taylor | 356/349 |
| 3,866,055 | 2/1975 | Pike | 356/349 |
| 3,930,733 | 1/1976 | Holly | 356/349 |
| 3,953,128 | 4/1976 | Holly | 356/349 |
| 4,154,529 | 5/1979 | Dyott | 356/342 |
| 4,251,733 | 2/1981 | Hirleman, Jr. | 356/335 |
| 4,329,054 | 5/1982 | Bachalo | 356/336 |
| 4,373,807 | 2/1983 | Gouesbet | 356/335 |
| 4,387,993 | 6/1983 | Adrian | 356/336 |
| 4,397,550 | 8/1983 | Matsuda et al. | 356/349 |
| 4,408,880 | 10/1983 | Tsuji et al. | 356/338 |
| 4,492,467 | 1/1985 | Drain et al. | 356/336 |
| 4,497,577 | 2/1985 | Sato et al. | 356/336 |
| 4,537,507 | 8/1985 | Hess | 356/336 |
| 4,596,036 | 6/1986 | Norgren et al. | 356/336 |
| 4,627,726 | 12/1986 | Turner | 356/336 |
| 4,633,714 | 1/1987 | Mazumder et al. | 356/336 |
| 4,662,749 | 5/1987 | Hatton et al. | 356/336 |
| 4,807,990 | 2/1989 | Keefer | 356/349 |
| 4,829,838 | 5/1989 | Clift et al. | 356/336 |
| 4,830,494 | 5/1989 | Ishikawa et al. | 356/336 |
| 4,918,699 | 4/1990 | Boyd et al. | 356/349 |
| 4,940,326 | 7/1990 | Tatsuno | 356/336 |
| 4,986,659 | 1/1991 | Bachalo | 356/336 |
| 5,017,008 | 5/1991 | Akiyama | 356/336 |
| 5,037,202 | 8/1991 | Batchelder et al. | 356/336 |
| 5,110,217 | 5/1992 | Sweeney | 356/349 |
| 5,160,976 | 11/1992 | Carr et al. | 356/336 |

OTHER PUBLICATIONS

K. Tatsuno and S. Nagao, Water Droplet Size Measurements In an Experimental Stream Turbine Using an Optical Fiber Droplet Sizer, Journal of Heat Transfer, Japan.

S. El Golli, G. Madelaine, P. Y. Turpin and J. Bricard, Recent Advances in Photoelectric Aerosol Measurements.

(Disclaimer) R. Johnson, Apparatus and Method for Detection and Characterization of Particles Using Light Scattered Therefrom, Los Alamos, N. Mex.

Saffman, Buchhave, and Tanger, Simultaneous Measurement of Size Concentration and Velocity of Spherical Particles By a Laser Dopplar Method.

Grehan and Gouesbet, Simultaneous Measurements of Velocities and Sizes of Particles in Flows Using a Combined System Incorporating a Top-hat Beam Techq.

W. M. Farmer, Measurement of Particle Size, Number Density, and Velocity Using a Laser Interferometer.

Walters and Skingley, an Optical Instrument for Measuring the Wetness Fraction and Droplet Size of Wet Steam Flows in LP Turbines, Leatherhead Surrey, UK.

Primary Examiner—Hoa Q. Pham
Attorney, Agent, or Firm—Edward A. Pennington; James M. Spicer; Harold W. Adams

[57] ABSTRACT

A wet steam monitor determines steam particle size by using laser doppler velocimeter (LDV) device to produce backscatter light. The backscatter light signal is processed with a spectrum analyzer to produce a visibility waveform in the frequency domain. The visibility waveform includes a primary peak and a plurality of sidebands. The bandwidth of at least the primary frequency peak is correlated to particle size by either visually comparing the bandwidth to those of known particle sizes, or by digitizing the waveform and comparing the waveforms electronically.

14 Claims, 3 Drawing Sheets

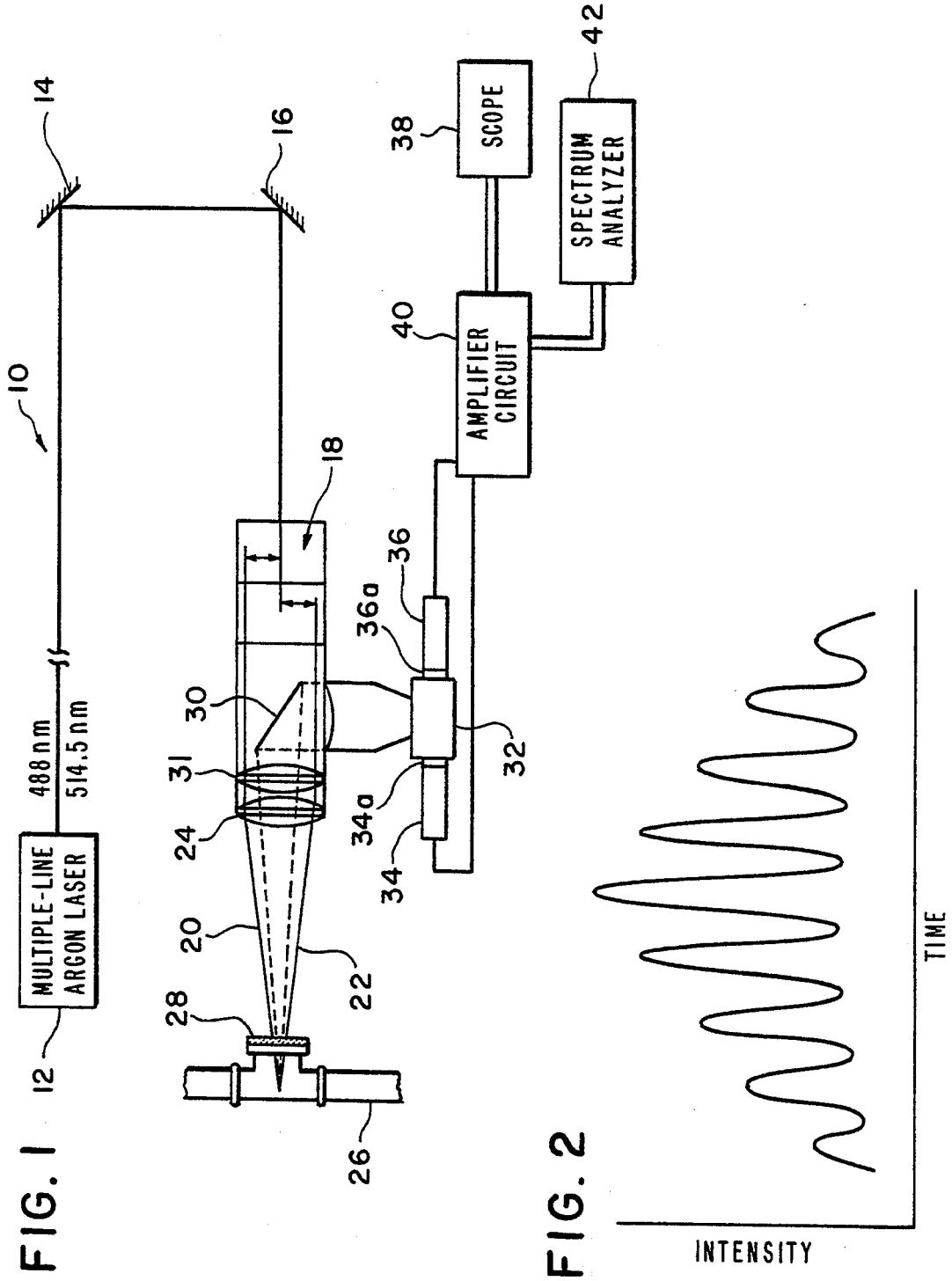

OPTICAL WET STEAM MONITOR

This invention was made with Government support under contract DE-AC05-84OR21400 awarded by the U.S. Department of Energy to Martin Marietta Energy Systems, Inc. and the Government has certain rights in this invention.

This is a continuation of co-pending application Ser. No. 07/928,340, filed on Aug. 12, 1992 now abandoned.

FIELD OF THE INVENTION

The present invention relates generally to the field of steam generation and, more specifically, to instrumentation and methods for non-invasive measurement of particle size and velocity of wet steam using a laser beam divided into two, equal-power coherent beams which are focused to a specific point within the steam environment through a single optical port.

BACKGROUND OF THE INVENTION

In steam plants using saturated steam, condensation due to energy losses results in a liquid phase in steam. Condensation begins as sub-micron size droplets on nucleation centers. Additional droplets may also be present at the output of the steam generator due to inefficiencies in the equipment intended to remove them. The droplets increase in size as the steam travels to the turbine, energy is lost, and condensation occurs. Droplets may also combine creating larger droplets. Droplets with a distribution of sizes and number densities will exist at any point in the wet steam and the distributions will change from point to point.

The resulting wet steam can cause damage to components of the steam system. For example, droplets entering a low pressure (LP) turbine can cause erosion, eventually resulting in the failure of turbine blades. Piping erosion caused by the droplets, in combination with corrosion, could lead to failure of the piping.

In view of the above, it is desirable to measure the liquid phase of steam to thus provide indications of premature failure in steam system components. Moreover, measurement of wet steam concentrations and velocities provides a viable estimate of turbine efficiency.

Optical instrumentation has been used in the past to measure particle size and velocity. Generally, the physical basis of optical detection in particle characterization is the scattering and absorption of light by the individual particles. Presently known devices for measuring particle size and velocity can be categorized as being based on single particle scattering or multiple particle scattering. In single particle scattering, the particle size, and/or velocity is determined for individual particles traversing a finite probe volume. Information about specific distributions of particles is obtained with statistical techniques from the individual particle events.

In multiple particle scattering, the scattered light from a large number of particles is measured to determine particle size and distribution. Measurements of scattering from multiple particles either use the extinction of light through a large probe volume or the angular dependency of Mie scattering to characterize the particles. An a priori assumption about the number-size density distribution function is usually necessary in multiple particle techniques.

Optical measurement of the liquid phase in steam was reported in a paper entitled "Determination of Droplet Sizes and Wetness Fraction in Two-Phase-Flows Using a Light-Scattering Technique (High Pressure Live Steam of Nuclear Power Plants, Low Pressure Steam Turbines, Cooling Tower Plumes) by A. Ederhof and G. Dibelius, *IMechE* 1976 (Conference Publication—Sixth Thermodynamics and Fluid Mechanics Convention, Durham, N.C.). For the light scattering probe described therein, a laser beam was focused into the steam flow of a live steam line. The liquid phase of the wet steam is thus characterized by measuring the intensity of light scattered at an angle of 90° from single particles interacting with a narrow collimated laser beam.

A multiple particle technique is described in "Water Droplet Size Measurements in an Experimental Steam Turbine Using an Optical Fiber Droplet Sizer" by K. Tatsuno and S. Nagao, *Journal of Heat Transfer*, Vol. 108/941 (November 1986). The optical droplet "sizer" described therein uses the forward scattering method, in which the angular sensitivity of Mie scattering was used to characterize multiple particles within a defined probe volume.

Another multiple particle technique is described in "An Optical Instrument for Measuring the Wetness Fraction and Droplet Size of Wet Steam Flows in LP Turbines" by P. T. Walters and P. C. Skingley, *I Mech E* 1979 (Conference Publication—Design Conference on Steam Turbines for the 1980's, London, United Kingdom). In this apparatus, multiple steam particles are characterized with a multi-wavelength extinction. The droplet size and wetness fraction of flows in LP steam turbines is obtained by measuring the optical transmission of a sample flowing through a slot in a probe body. Data generated thereby is interpreted from light scattering theory to give values for size and distribution.

In general, the instrumentation devices described above are sensitive to unwanted scattering outside of the probe volume. Each device isolated the optical probe volume from extraneous scattering by containing the probe volume within a radial arm extending into the steam environment. The measured scatter signal was transmitted using various optical techniques, such as fiber optics, through the radial arm to photodetectors located outside the steam pipe. Measurements were made at different radial locations within the steam environment by moving the radial arm. Measured particle sizes ranged from 0.1 $\mu$m to 500 $\mu$m under a variety of conditions. Most measured particle sizes in LP turbines were in the 0.8 $\mu$m range.

A problem inherent to the type of instrumentation described above is that they are invasive. In addition to the problem of placing a radial arm through the wall of a steam pipe, problems are encountered in determining the effect of the radial arm on the steam flow and therefore on the measurement itself. As a result, a large variability in steam particle sizes have thus been measured under similar conditions.

Another problem is related to the way in which the scattered light is analyzed. The aforementioned instrumentation are designed to measure phase shift of the scattered light at different radial locations as a particle traverses the probe volume. For example, see "Simultaneous Measurement of Size, Concentration and Velocity of Spherical Particles by a Laser Doppler Method" by M. Saffman et al. (paper presented at The Second International Symposium on Applications of Laser Anemometry to Fluid Mechanics, Jul. 2-4, 1984, Lisbon).

These instruments require several independent views of the probe volume and thus dictate either an arm extending into the steam environment or the use of multiple ports in the steam pipe or turbine housing. However, when making measurements of process steam, it is desirable to minimize the number of access ports to the environment. This is necessary not only from a logistics standpoint with the difficulty in the initial set-up and alignment of multiple optical ports, but also from a maintenance standpoint in keeping the optics aligned in the presence of large vibration sources and thermal stresses.

SUMMARY OF THE INVENTION

An object of the present invention is to provide an optical wet steam monitor which is capable of making measurements while being non-invasive and using only a single optical port.

Another object of the present invention is to provide an optical wet steam monitor which is capable of measuring size and velocity of wet steam particles through a single optical port.

These and other objects of the invention are met by providing an optical wet steam monitor which includes means for producing two, equal power coherent light beams, means for focusing the two beams at a point of intersection within a steam environment, each beam having two spectral components, a fringe pattern being formed at the point of intersection due to optical path length differences in the two beams, means for collecting backscattered light from a single particle passing through the fringe pattern, means for isolating the two spectral components from the collected backscattered light and focusing the respective spectral components on corresponding light detectors, means for producing a frequency domain visibility waveform having a primary frequency peak and a plurality of sidebands, and means for correlating a bandwidth of at least the primary frequency peak to a particle size.

Other objects, advantages and salient features of the invention will become apparent from the following detailed description, which, taken in conjunction with the annexed drawings, discloses preferred embodiments of the invention.

BRIEF DESCRIPTION OF THE DRAWINGS

FIG. 1 is a schematic view of an optical wet steam monitor according to a preferred embodiment of the present invention;

FIG. 2 is a graph showing a typical backscattered signal intensity as a function of time obtained with a laser doppler velocimeter.

DETAILED DESCRIPTION OF THE PREFERRED EMBODIMENTS

Figure 3A:
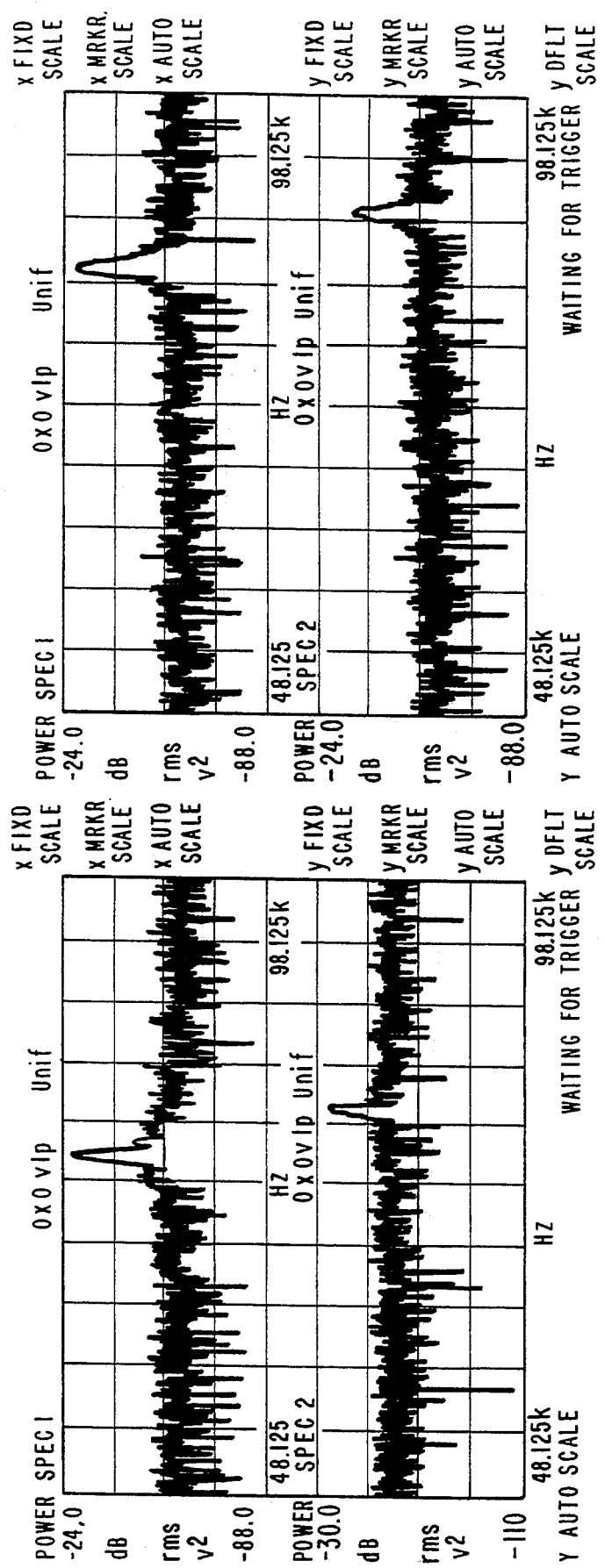
FIGS. 3(a) and 3(b) are displays of visibility waveforms in the frequency domain as produced by a spectral analyzer, for 0.22 $\mu$m diameter and 4.03 $\mu$m latex particles, respectively.

Referring to FIG. 1, an optical wet steam monitor 10 includes a laser source 12 which produces a laser output beam. In a particularly preferred embodiment, the laser source 12 is a multiple-line argon-ion laser working in the TEMoo mode. Such laser sources are available from SPECTRA-PHYSICS, as model 168-04. To reduce the length of the device, mirrors 14 and 16 are used to turn the laser beam 180°.

A beam splitter 18 divides the laser output beam into two, equal power, coherent beams. Each beam contains two spectral lines. For the preferred argon ion laser source, the two spectral lines are at 488 nm and 514.5 nm. Although the preferred laser source has two spectral lines, other sources having a single spectral line may be used. The resulting two beams 20 and 22 are then focused by an achromatic forward lens 24 to a specific point within a particle-containing environment. A focusing mirror could be used in place of the lens 24. In the case of wet steam monitoring in a steam generator plant, a steam pipe 26 is provided with a single optical port 28. Other structures could be provided with optical ports for sensing, such as the low pressure (LP) turbine housing. Areas of high and low intensity, or fringe pattern, are formed due to the optical path length differences in the two beams at the point of intersection of the beams 20 and 22.

The backscattered light from a single particle passing through the resulting fringe pattern is collected by a backscatter collector lens 30 and focused onto a color separator 32. A beam expander 31 may be provided between the forward lens and the backscatter collector lens 30 to enhance the backscatter light signal. Beam expanders are commercially available from Dantec Electronics Inc. of Mahwah, N.J. The color separator 32 may include a dichroic mirror, for example. The two spectral components are isolated by the color separator 32 and each component is focused onto a corresponding photomultiplier tube 34 and 36 after passing through narrowband filters 34a and 36a, respectively.

Generally, the apparatus described above, except for the application to wet steam monitoring through a single port, corresponds to a standard laser doppler velocimeter (LDV), and as such, the various components are commercially available. While LDV's have been used to measure velocity and particle size, they have not been applied to commercial steam facilities. Moreover, they generally require multiple ports and rely on forward scattering measurements. Most commercial LDV's use phase information rather than visibility, although Farmer first suggested using visibility to extract particle size. See, W. M. Farmer, "Measurement of Particle Size, Number Density, and Velocity Using a Laser Interferometer", *Applied Optics*, Vol. 11, p.2603, (1972). In the present case, the use of backscatter data avoids the requirement for a second port.

The present invention also differs from the past uses of LDV's in the way the scatter signal is processed. A typical backscattered signal obtained with a LDV is shown in FIG. 2. The signal can be produced with a standard oscilloscope 38 coupled to an amplifier circuit 40. The signal contains both particle size and velocity information. Commercially available LDV's obtain particle velocity information by transforming the time waveform to the frequency domain and measuring the center frequency of the resulting peak. In the past, size information has been derived from either the maximum amplitude of the signal (so called "pedestal calibration"), the difference between the intensity of the scattered signal from a bright fringe and that of the next consecutive dark fringe divided by the sum of the intensities ("visibility"—see W. M. Farmer article noted above), or the phase shift of the signal measured by multiple optical receivers located at specific angles relative to the plane of the probe volume ("phase doppler"). Thus, prior techniques to extract particle size from visibility waveforms have derived the information from the time waveforms.

Figure 3B:
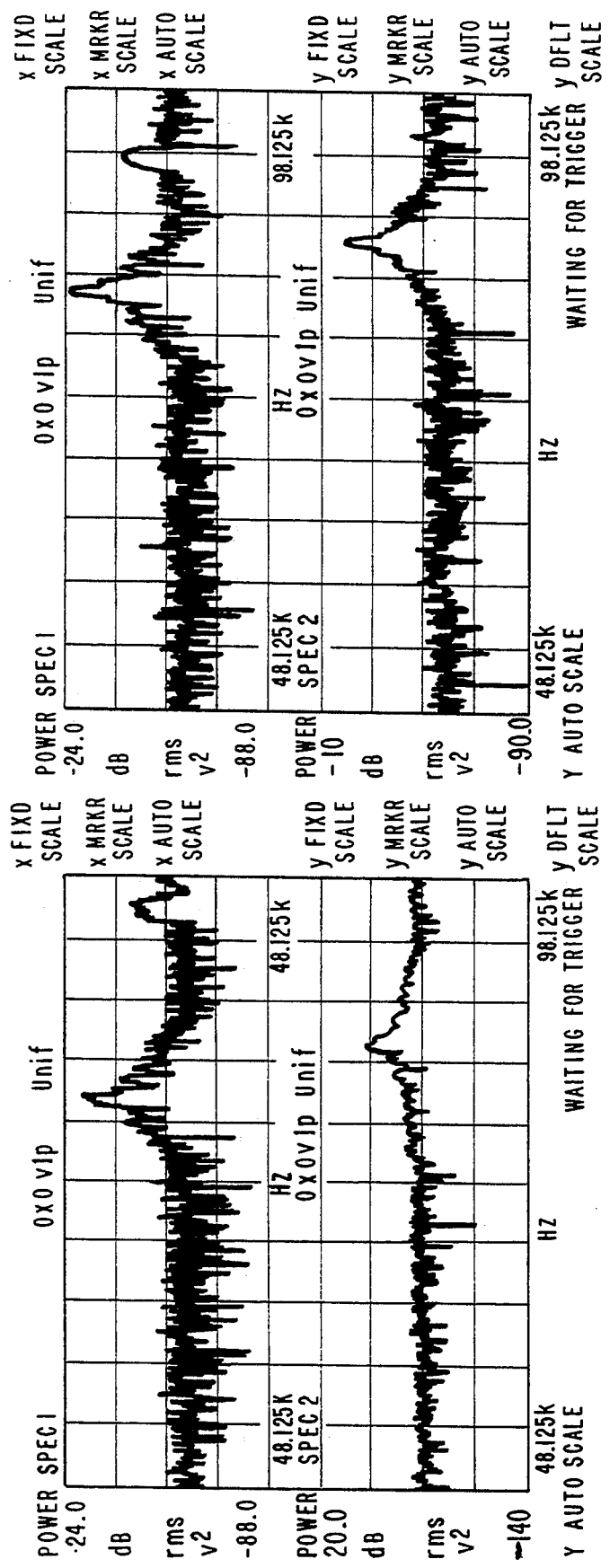

The present invention obtains size information from the spectral characteristics, which vary in accordance with variations in particle size. The particle size is characterized by observing the bandwidth of the primary frequency peak as well as the magnitudes and bandwidths of any sidebands appearing in the signal. Particle size determination is achieved by correlating the spectral characteristics of the signal with those of specific particle sizes which have been obtained through either theoretical models or empirical data. In order to accomplish this, a digital signal analyzer or spectral analyzer 42 is coupled to the amplifier circuit 40, either to replace the oscilloscope 38 or to be used in conjunction therewith. The spectrum analyzer is commercially available from Hewlett-Packard, among others. The analyzer produces a display based on a Fourier transform as illustrated in FIGS. 3(a) and 3(b), although Fourier transform is not the only available diagnostic program. Other analyzers may be employed, including those customized for the present purposes. For example, a spectrum analyzer typically produces a visual display. According to the present invention, the spectrum analyzer could be programmed to digitize the frequency "signatures" of each particle. These digitized signals can be compared electronically rather than visually to provide particle size determination. In that regard, a digital or analog read-out of particle size would replace the visual screen seen in FIGS. 3(a) and (b).

FIGS. 3(a) and 3(b) illustrate visibility waveforms in the frequency domain, as screen read-outs of the spectral analyzer 42. Latex particles of known size were used experimentally to demonstrate the relationship between particle size and bandwidth. This correlation allows one to determine particle size. Visibility waveforms for latex particles having a known diameter of 0.22 µm were produced by the spectrum analyzer 42 and illustrated in FIG. 3(a). The top trace is for the 514.5 nm spectral line, and the bottom trace is for the 488 nm spectral line. Visibility waveforms for latex particles having a known diameter of 4.03 µm were produce and illustrated in FIG. 3(b). Again, the top trace is for the 514.5 µm spectral line and the bottom trace is for the 488 µm spectral line.

For the 0.22 µm particle shown in FIG. 3(a), a very sharp peak at the central frequency is observed with only slight evidence of the formation of side bands in the upper (514.5 nm) trace. Referring to FIG. 3(b), as the particle size increases from 0.22 µm to 4.3 µm, there is an observable broadening of the central peak, and a tendency for sidebands to form. Based on other particle sizes tested, it was observed that the area under the central peak and associated sidebands appears to increase monotonically with particle size, although the increase in area is less pronounced than the general broadening of the frequency domain signal.

By making visibility measurements in the frequency domain, inaccuracies typical of visibility and pedestal measurements of particles less than 0.8 µm in diameter may be reduced due to the increased ability to isolate the signal of interest from system noise. Moreover, it is possible to use the two independent measurements of the same event (multiple wavelengths) to enhance the accuracy of the measurement. In addition, since the number of fringes in the LDV probe volume and the average particle velocity are known quantities in a steam measurement, valid in-plane measurements can be distinguished from invalid out of plane waveforms in turbulent flow by examining the center frequency of the resulting peak. Thus, frequency domain visibility measurements according to the present invention provide greater accuracy and resolution compared to time domain analysis.

The present invention can be adapted for use in measuring particle size, distribution and velocity for particles other than wet steam. Generally, the invention can be used in any environment to measure sub-micron and micron sized particles where access is restricted and measurements need to be made without invasively exposing the particle environment. The system will have particularly advantageous results for use in fossil fuel and nuclear power plants to evaluate the size and velocities of steam particles at various locations in the system. It will also be possible to combine the information gathered by the monitor of the present invention with other sensor outputs to evaluate turbine efficiencies on-line.

While advantageous embodiments have been chosen to illustrate the invention, it will be understood by those skilled in the art that various changes and modifications can be made therein without departing from the scope of the invention as defined in the appended claims.

What is claimed is:

1. An optical wet steam monitor comprising:
   a laser source having a laser output;
   a beam splitter receiving the laser output and generating therefrom two equal power, coherent beams, each beam having at least one spectral line;
   means for focusing the two beams at a point of intersection within a steam environment, optical path length differences in the two beams at the point of intersection forming a fringe pattern, and a single particle of steam passing through the fringe pattern producing backscattered light;
   means for converting the backscattered light into an electrical signal;
   signal processing means, receiving the electrical signal from the converting means, for producing a frequency domain waveform having a primary frequency peak and a plurality of sidebands associated with the primary frequency peak; and
   means for correlating a bandwidth of the primary peak and the plurality of sidebands to a specific particle size.

2. An optical wet steam monitor according to claim 1, wherein the laser source is an argon-ion laser, and the two spectral lines are at 488 nm and 514.5 nm.

3. An optical wet steam monitor according to claim 1, wherein the focusing means comprises a positive lens.

4. An optical wet steam monitor according to claim 3, wherein the converting means comprises color separator means for isolating the two spectral components of the backscattered light and focusing each component onto a corresponding photomultiplier tube, backscatter light collector means, disposed in the optical path of the backscattered light, for focusing the backscattered light into the color separator means, each photomultiplier tube producing a corresponding electrical signal for each spectral line which is fed to the signal processing means.

5. An optical wet steam monitor according to claim 4, further comprising a beam expander disposed between the positive lens and the backscatter light collector means.

6. An optical wet steam monitor according to claim 1, wherein the signal processing means comprises a spectrum analyzer.

7. An optical wet steam monitor according to claim 1, wherein the bandwidth of the primary peak varies in accordance with particle size.

8. An optical wet steam monitoring system comprising:
   a single optical port disposed in a wall of a structure which contains a steam environment;
   a laser source having a laser output;
   a beam splitter receiving the laser output and generating therefrom two equal power, coherent beams, each beam having at least one spectral line;
   means for focusing the two beams at a point of intersection within a steam environment through the single optical port, optical path length differences in the two beams at the point of intersection forming a fringe pattern, and a single particle of steam passing through the fringe pattern producing backscattered light;
   means for converting the backscattered light into an electrical signal;
   signal processing means, receiving the electrical signal from the converting means, for producing a frequency domain waveform having a primary frequency peak and a plurality of sidebands associated with the primary frequency peak; and
   means for correlating a bandwidth of the primary peak and the plurality of sidebands to a specific particle size.

9. An optical wet steam monitoring system according to claim 8, wherein the laser source is an argon-ion laser, and the two spectral lines are at 488 nm and 514.5 nm.

10. An optical wet steam monitoring system according to claim 8, wherein the focusing means comprises a forward lens.

11. An optical wet steam monitor according to claim 10, wherein the converting means comprises color separator means for isolating the two spectral components of the backscattered light and focusing each component onto a corresponding photomultiplier tube, backscatter light collector means, disposed in the optical path of the backscattered light, for focusing the backscattered light onto the color separator means, each photomultiplier tube producing a corresponding electrical signal for each spectral line which is fed to the signal processing means.

12. An optical wet steam monitoring system according to claim 11, further comprising a beam expander disposed between the forward lens and the backscatter light collector means.

13. An optical wet steam monitoring system according to claim 8, wherein the signal processing means comprises a spectrum analyzer.

14. A method for measuring particle size of micron and sub-micron sized particles flowing in an enclosure comprising:
   producing a laser beam having at least one spectral line;
   splitting the laser beam into two beams;
   focusing the two beams at a point of intersection within the enclosure through a single optical port, optical path length differences in the two beams at the point of intersection forming a fringe pattern, and a single particle of steam passing through the fringe pattern producing backscattered light;
   converting the backscattered light into an electrical signal;
   producing a frequency domain waveform having a primary frequency peak and a plurality of sidebands associated with the primary frequency peak; and
   correlating a bandwidth of the primary peak and the plurality of sidebands to a specific particle size.

* * * * *